US012758295B2

(12) United States Patent
Ellman et al.

(10) Patent No.: US 12,758,295 B2
(45) Date of Patent: Oct. 13, 2026

(54) ELECTROSURGICAL SYSTEM FOR SURFACE TISSUE TREATMENT

(71) Applicants: Spencer Ellman, Long Island City, NY (US); Alan Ellman, Baldwin, NY (US); Scott Goldsmith, Woodmere, NY (US)

(72) Inventors: Spencer Ellman, Long Island City, NY (US); Alan Ellman, Baldwin, NY (US); Scott Goldsmith, Woodmere, NY (US)

( * ) Notice: Subject to any disclaimer, the term of this patent is extended or adjusted under 35 U.S.C. 154(b) by 260 days.

(21) Appl. No.: 18/403,124

(22) Filed: Jan. 3, 2024

(65) Prior Publication Data

US 2025/0213288 A1 Jul. 3, 2025

(51) Int. Cl.

*A61B 18/12* (2006.01)
*A61B 18/14* (2006.01)
*A61B 18/00* (2006.01)

(52) U.S. Cl.

CPC .......... *A61B 18/1233* (2013.01); *A61B 18/14* (2013.01); *A61B 2018/00083* (2013.01); *A61B 2018/00178* (2013.01); *A61B 2018/1407* (2013.01)

(58) Field of Classification Search

CPC . A61B 18/1233; A61B 18/14; A61B 18/1402; A61B 2018/00083; A61B 2018/00178; A61B 2018/00601; A61B 2018/1407

See application file for complete search history.

(56) References Cited

U.S. PATENT DOCUMENTS 3,532,095 A * 10/1970 Miller ................ A61B 18/1402 606/49
5,261,905 A * 11/1993 Doresey, III ....... A61B 18/1482 606/49
6,168,593 B1 * 1/2001 Sharkey ............... A61B 18/148 606/34
6,994,707 B2 * 2/2006 Ellman .................. A61B 18/12 606/42
11,051,872 B2 7/2021 Stanley, II
2004/0064139 A1 * 4/2004 Yossepowitch .............................. A61B 17/320016 606/46
2005/0222567 A1 * 10/2005 Ouchi ................ A61B 18/1492 606/45
2006/0064084 A1 * 3/2006 Haemmerich ..... A61B 18/1477 606/41
2008/0027428 A1 * 1/2008 Palanker ............ A61B 18/1402 606/45
2009/0069802 A1 * 3/2009 Garito .................... A61B 18/14 606/49
2010/0049229 A1 * 2/2010 Archambault ..... A61B 17/3213 606/167

(Continued)

*Primary Examiner* — Daniel W Fowler

(57) ABSTRACT

An electrosurgical system, comprising a handpiece having a mounting channel therein, an electrical contact in communication with the mounting channel; and an electrode arrangement that is engageable within the mounting channel. The electrode arrangement further comprises a mounting shaft that is in communication with an active electrode end, that is configured to deliver RF energy when the mounting shaft is in electrical engagement with the electrical contact within the mounting channel and the handpiece is in an energized state. The active electrode end includes at least one edge portion that includes a visual indicator of a treatment depth.

10 Claims, 9 Drawing Sheets

(56) References Cited

U.S. PATENT DOCUMENTS

| | | | | |
|---|---|---|---|---|
| 2011/0196366 | A1* | 8/2011 | Humble ............ | A61B 18/1482<br>606/37 |
| 2014/0276770 | A1* | 9/2014 | Ellman ............. | A61B 18/1477<br>606/34 |
| 2018/0256139 | A1* | 9/2018 | Miller .................... | A61B 18/14 |
| 2018/0360529 | A1* | 12/2018 | Brannan ............ | A61B 18/1815 |

* cited by examiner

ELECTROSURGICAL SYSTEM FOR SURFACE TISSUE TREATMENT

TECHNICAL FIELD

The present disclosure relates generally to electrosurgical devices and methods of using same, and more specifically to electrosurgical systems utilizing such electrosurgical devices.

BACKGROUND

Electrosurgical instruments are well known and widely used in the medical, dental, and veterinary fields. Such instruments many generate electrical currents in the RF spectrum which are used to deliver power to hand-held surgical instruments incorporating one or more electrode components and are used to perform surgical procedures such as tissue cutting, coagulation, hemostasis and other electrosurgical applications.

Electrosurgical instruments may include a unit for generating RF power which is delivered to hand-held surgical instruments to activate electrodes incorporated into the instruments to perform a procedure. Such units may be a console-type to house circuitry for RF power generation and to provide input and output connections from such circuitry to a variety of external devices including a power supply and hand-held surgical instruments. A console unit may include interactive display and input panels for user-operation of the electrosurgical instruments. Input panels may be provide switches, buttons, touch screens, IR controls and the like to allow a user to select and input operating conditions in order to activate the electrosurgical tool for a desired surgical operation or procedure. Examples of a suitable console unit may be found in U.S. Pat. No. 10,456,189, the contents of which are incorporated by reference in it entirety.

The electrodes of the surgical devices can be used in various surgical procedures in which a conventional scalpel is employed, for example for general cutting procedures. Electrodes provide an advantage of providing electrosurgical currents at the cutting edge of a scalpel, which assists in cutting tissue while at the same time providing a coagulation effect.

SUMMARY

In one exemplary arrangement, an electrosurgical system is disclosed that comprises a handpiece having a mounting channel therein, an electrical contact in communication with the mounting channel; and an electrode arrangement that is engageable within the mounting channel. The electrode arrangement further comprises a mounting shaft that is in communication with an active electrode end, that is configured to deliver RF energy when the mounting shaft is in electrical engagement with the electrical contact within the mounting channel and the handpiece is in an energized state. The active electrode end includes at least one edge portion that includes a visual indicator of a treatment depth.

In one exemplary arrangement, the mounting shaft may further comprise a malleable section that permits selective positioning of the active electrode end with respect to the handpiece.

An insulating sleeve may be disposed over the mounting shaft. When positioned, a proximal end of the mounting shaft extends outwardly from the insulating sleeve when mounted on the mounting shaft. In one exemplary arrangement, the insulating sleeve may be heat-shrunk onto the mounting shaft. Once the insulating sleeve is position on the mounting sleeve, the insulating sleeve and mounting shaft are positioned within the mounting channel.

In one exemplary arrangement, the mounting shaft may be locked within the mounting channel of the handpiece. For example, in one exemplary arrangement, the mounting shaft may include a pair of mounting grooves that cooperate with a locking element disposed on a distal end of the handpiece to lock the electrode arrangement within the handpiece.

Disposed within the mounting channel is an electrical contact that provides electrical energy to the electrode assembly. In one exemplary arrangement, the electrical contact is constructed as a tubular member disposed within the mounting channel so as to encircle a proximal end of the mounting shaft when the mounting shaft is seated within the mounting channel.

The electrosurgical system may further comprise a console generator that is configured to power the handpiece. The console generator connects to the handpiece via an electrical cable, with a first end of the electrical cable being connected to an electrical contact disposed within the handpiece. The first end of the electrical cable may be selectively connected to the handpiece. A second end of the electrical cable may comprise a smart plug that operatively serves to limit the electrical output to the handpiece from the console generator.

In one exemplary arrangement, the active electrode end is configured in the shape of an oval. Further, the active electrode end may be configured to be concave shaped, with the edge portion being disposed about the periphery of the active electrode end. A bottom outer surface of the active electrode end may be insulated.

In one exemplary arrangement, the active electrode end is configured with a circular shape and further includes an opening therethrough. An edge band may extend around the outer periphery of the active electrode end. In one arrangement, the active electrode end is angled with respect to a central axis extending through the mounting shaft such that a distal most end of the active electrode end is positioned higher than the mounting shaft.

In another exemplary arrangement, the active electrode end is in the form of a cantilever beam. The cantilever beam may be peaked, with edge sections disposed on either side of a center line that extends through the cantilever beam. In one exemplary arrangement, a distal end of the cantilever beam may be offset such that the cantilever beam extends at an angle from a center line extending through the mounting beam, when viewed in plan view.

BRIEF DESCRIPTION OF THE DRAWINGS

Exemplary arrangement of the present disclosure will now be described in greater detail with reference to the attached figures, in which.

DETAILED DESCRIPTION

Figure 1:
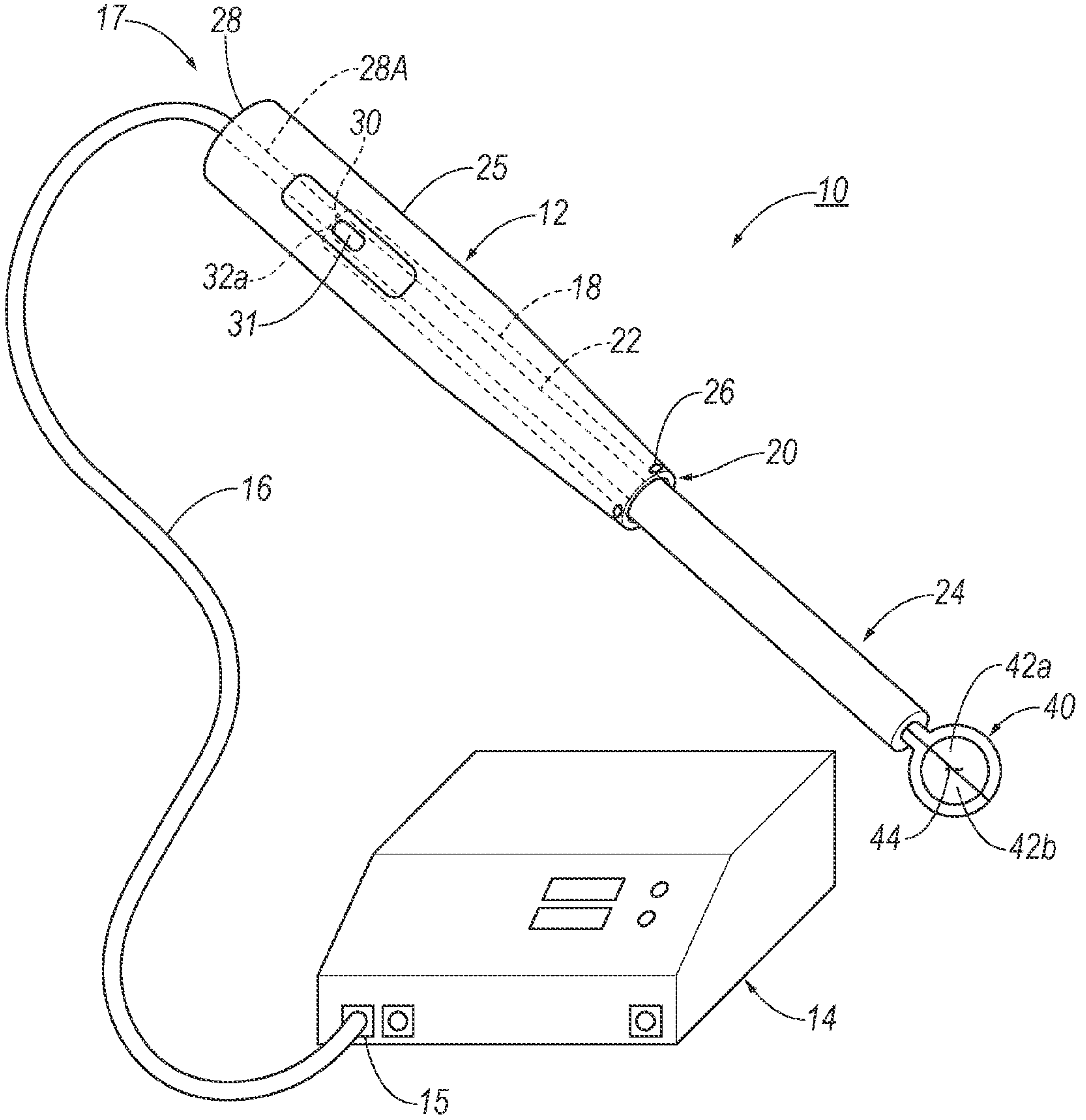
FIG. 1 is a schematic, perspective view of an exemplary arrangement of an electrosurgical system according the disclosure.

Referring now to the discussion that follows, and to the drawings, illustrative approaches to the disclosed systems and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

With reference to FIG. 1, an exemplary arrangement of an electrosurgical system 10 is shown. In one exemplary arrangement, the electrosurgical system 10 includes a handpiece 12 and an electrosurgical console generator 14. An electrical cable 16 operatively connects the console generator 14 to the handpiece 12. In one exemplary arrangement, the electrical cable 16 is removably attachable to the handpiece.

The handpiece 12 is defined by a proximal end 17 and a distal end 20. The distal end 20 includes an opening for a mounting channel 18 therein that is configured to receive a mounting shaft 22 of an electrode arrangement 24, which will be explained in further detail below.

The electrosurgical console generator 14 may be any suitable electrosurgical apparatus that is configured to deliver radiofrequency energy to the handpiece 12. For example, the console generator 14 may be operable to selectively generate and deliver alternating polarity electrical current. In some exemplary arrangements, the console generator 14 provides power to the handpiece 12 at a high operating frequency, for example, within a range of approximately 2 to 4 MHZ, although other suitable operating frequencies are contemplated.

Referring now to FIG. 1, in one exemplary arrangement, the handpiece 12 includes a handle section 25 and a locking element 26. The mounting channel 18 extends from an opening in the distal end 20 toward the proximal end 17, within the handle section 24. Disposed within the mounting channel 18 is an electrical contact. The electrical contact 28 is operatively connected to, and receives power from, the electrical cable 16. In one exemplary arrangement, the electrical contact 28 may be a tubular member. However, in another exemplary arrangement, the electrical contact 28A may be disposed at a proximal end 30 of the mounting channel 18 such that when the mounting shaft 20 is properly seated within the mounting channel 18, the electrical contact 28A is engaged with a corresponding electrical contact 32A disposed on a proximal end of the mounting shaft 22.

A first exemplary arrangement of an electrode arrangement 24 is disclosed in FIGS. 2-5. The exemplary electrode arrangement 24 includes an electrode member 34 and an insulation sleeve 36. The electrode member 34 is constructed of an electrically conductive material or materials, such as a metallic materials.

Figure 2:
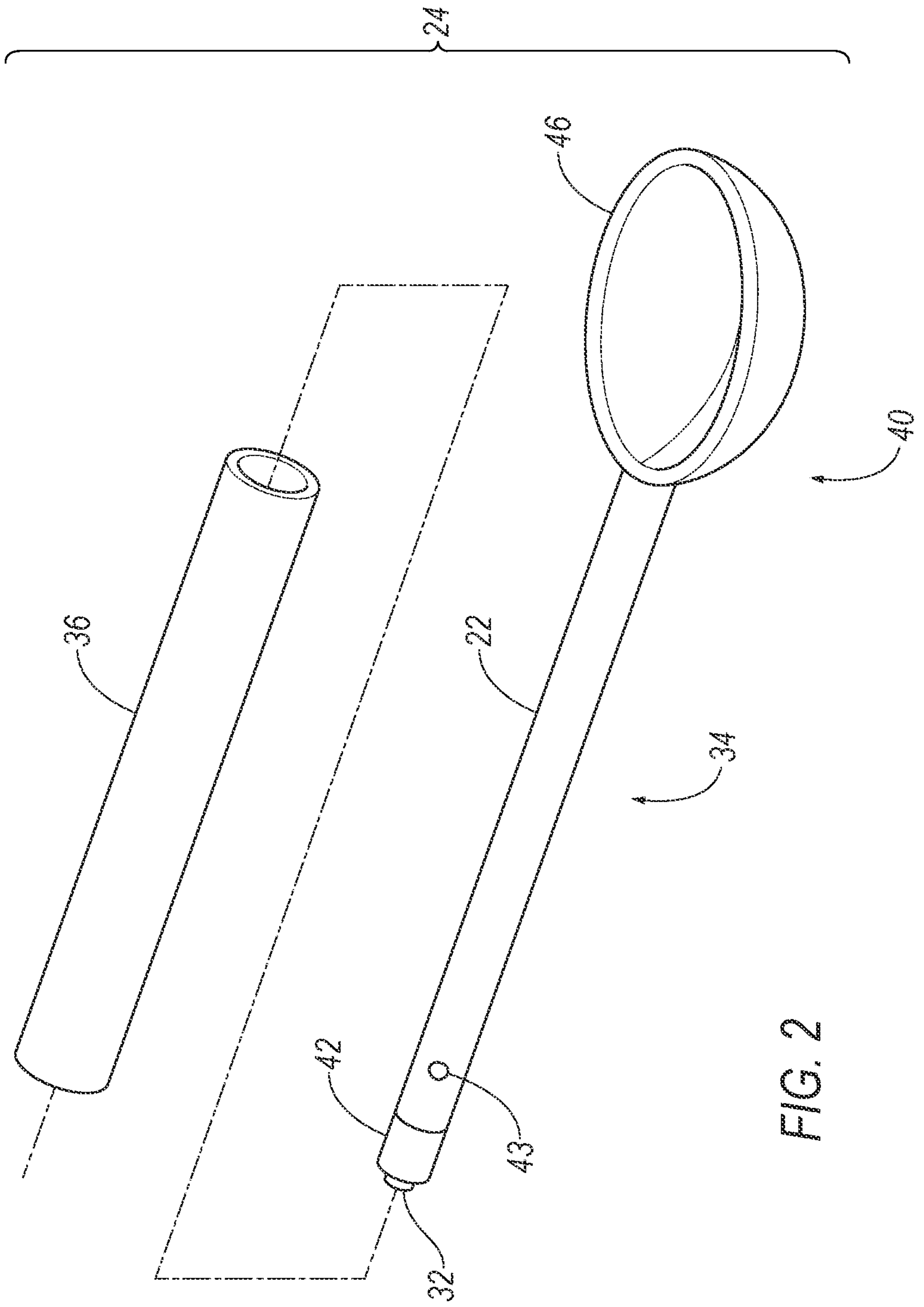
FIG. 2 is partially exploded view of an exemplary arrangement of an electrosurgical hand-piece.
Figure 3:
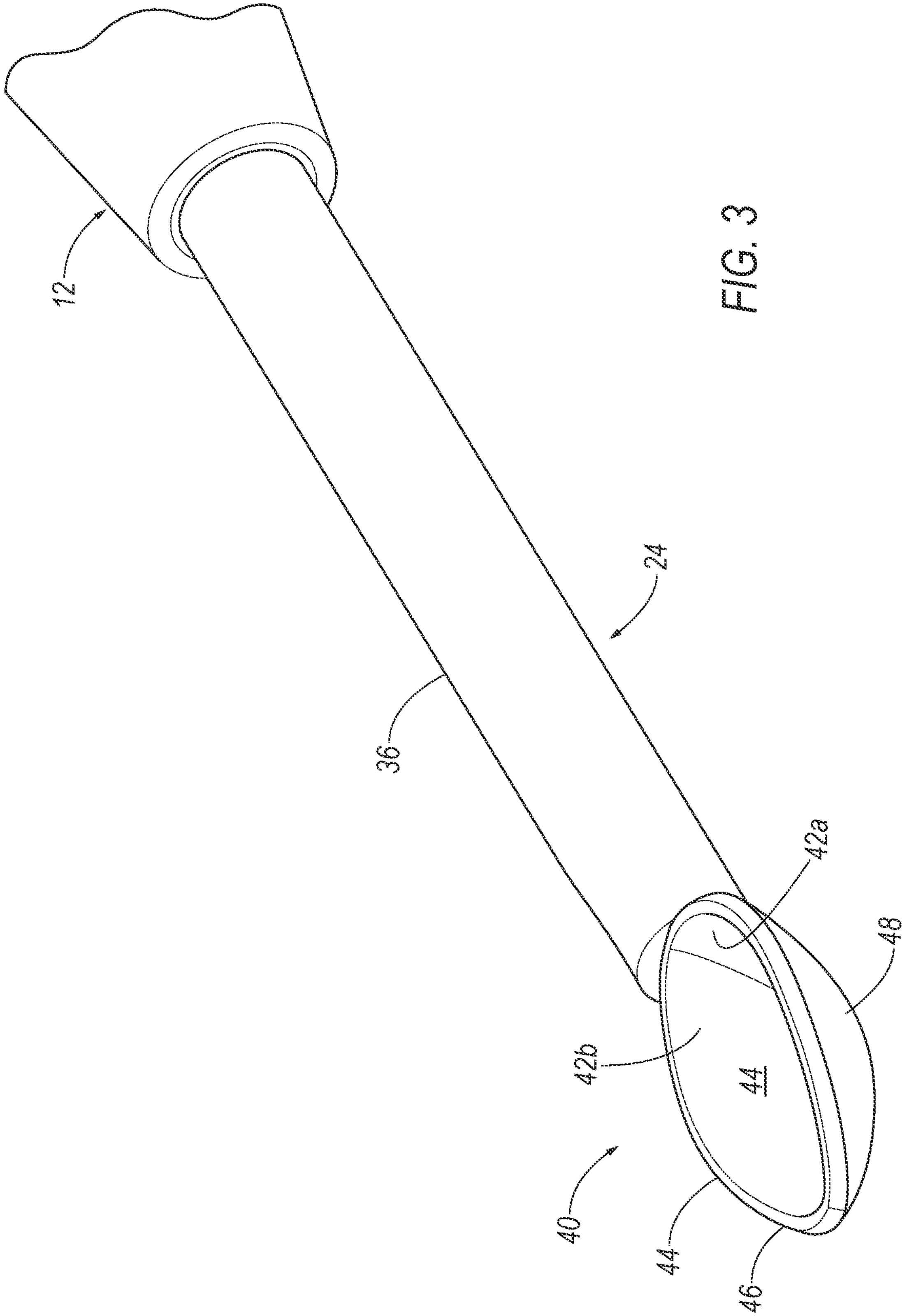
FIG. 3 is perspective view of an exemplary arrangement of an electrode arrangement that may be utilized in the electrosurgical system.
Figure 4:
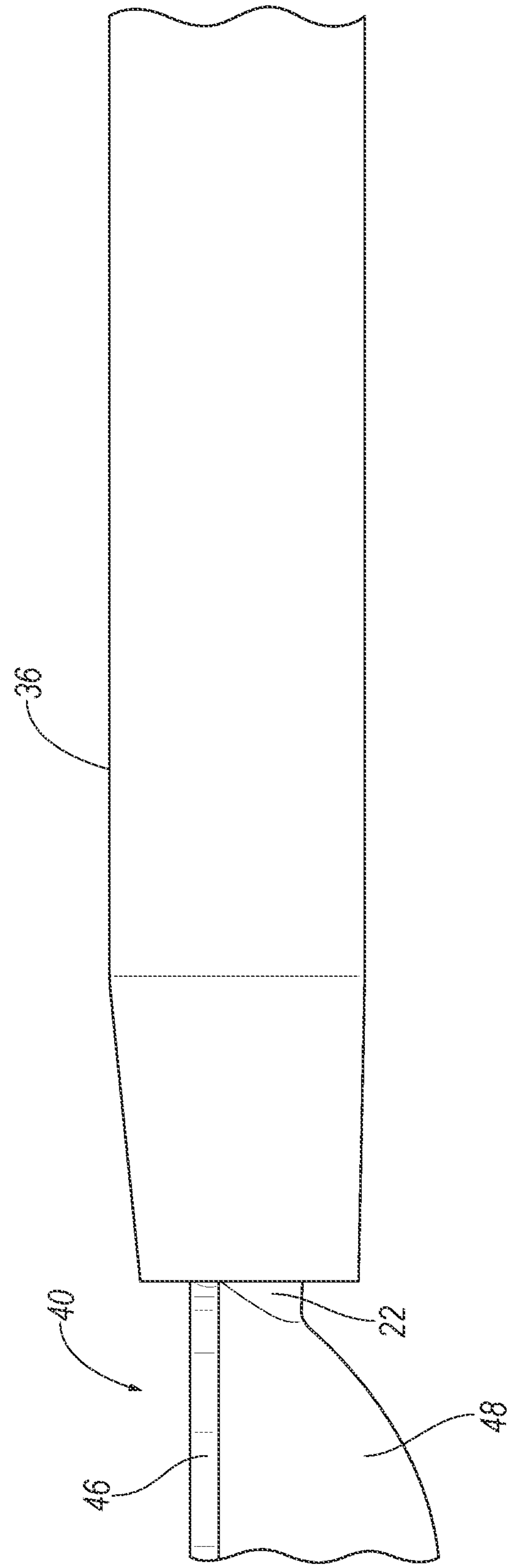
FIG. 4 is a side view of the electrode arrangement of FIG. 3.
Figure 5:
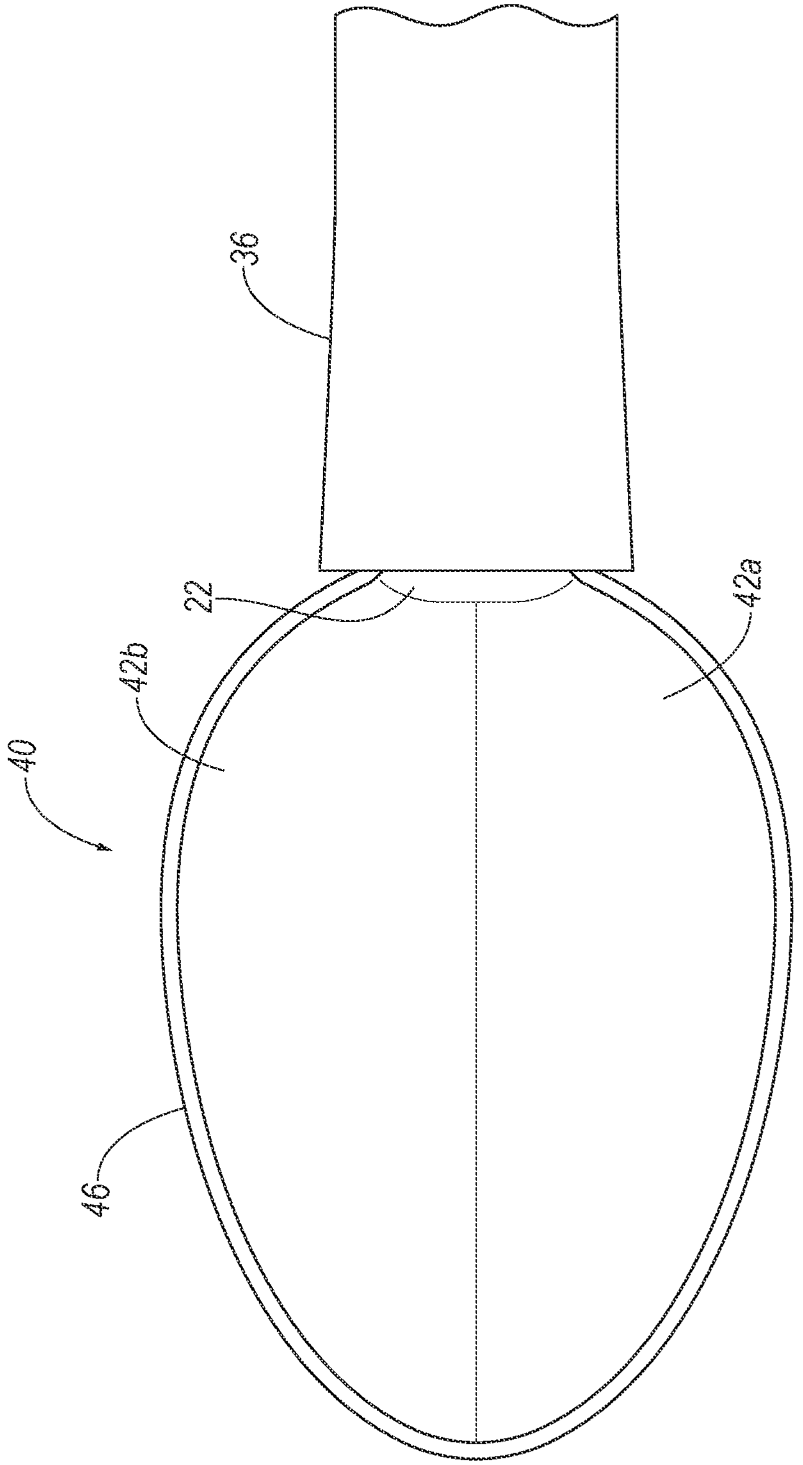
FIG. 5 is a top view of the electrode arrangement of FIG. 3.

In contrast to the electrode member 34, the insulation sleeve 36 is formed of an electrically insulating material or materials. In one exemplary arrangement, the insulation sleeve 36 is formed as a separate hollow component, as shown in FIG. 2, into which a mounting shaft 22 of the electrode member 34 may be inserted. In another exemplary arrangement, the insulation sleeve 36 may be applied as a coating directly to the mounting shaft 22. The insulating sleeve 36 may be constructed of a polymeric material, or other suitable non-conductive material. The insulation sleeve 36 is sized to extend to an active electrode end 40, when installed on the mounting shaft 22, such that only the active electrode end 40 is exposed during a procedure. A proximal end 42 of the mounting shaft 22 will remain exposed from the insulating sleeve 36 when the insulating sleeve 36 is positioned on the mounting shaft 22. The exposed proximal end 42, which carries electrical contact 32, will engage with the electrical contact 28/28A disposed within the mounting channel 18 of the handpiece 12 so as to energize the electrode arrangement 24.

In one exemplary arrangement, the mounting shaft 22 may include engagement grooves, one of which 43 is shown in FIG. 2. When the electrode arrangement 24 is engaged within the mounting channel 18 of the handpiece 12, the locking element 26 may engage with the engagement grooves 43 of the mounting shaft 22 to secure the electrode arrangement 24 within the handpiece 12.

In one exemplary arrangement, the active electrode end 40 is constructed to have an oval or spoon shape, as shown in FIGS. 2-5. Moreover, the active electrode end 40 is also constructed to be concave, with a positive and negative electrodes 42*a*, 42*b*. For example, an active surface 44 of the electrodes is formed jointly from the positive and negative electrodes 42*a*, 42*b*, which is concave. A scraping edge 44 is defined by an edge band 46 disposed around a periphery of an active electrode end 40. In one exemplary arrangement, the edge band 46, may further include indicia on a portion of the edge band 46. The indicia may be used to visually indicate a depth of ablation when the active electrode end 40 is applied to tissue. The indicia may be in any form, i.e., the edge band 46 may be provided with etched depth markers, or may be colorized to visually indicate the depth when applied to tissue. In one exemplary arrangement, a bottom outer portion 48 (i.e., a convex outer surface) of the active electrode end 40 may be insulated so as to prevent unintentional application during us of the electrosurgical system 10. For example, the convex outer surface 48 may be coated with PTFE.

Alternatively, as will be explained in further detail below, the convex outer surface/outer portion 48 may be uninsulated so as to permit use as a treatment surface. For example, in one exemplary arrangement, the electrode end may have a conductive gold plating or titanium nitride. This material may also be used for other electrode arrangements, to be discussed below.

Figure 6A:
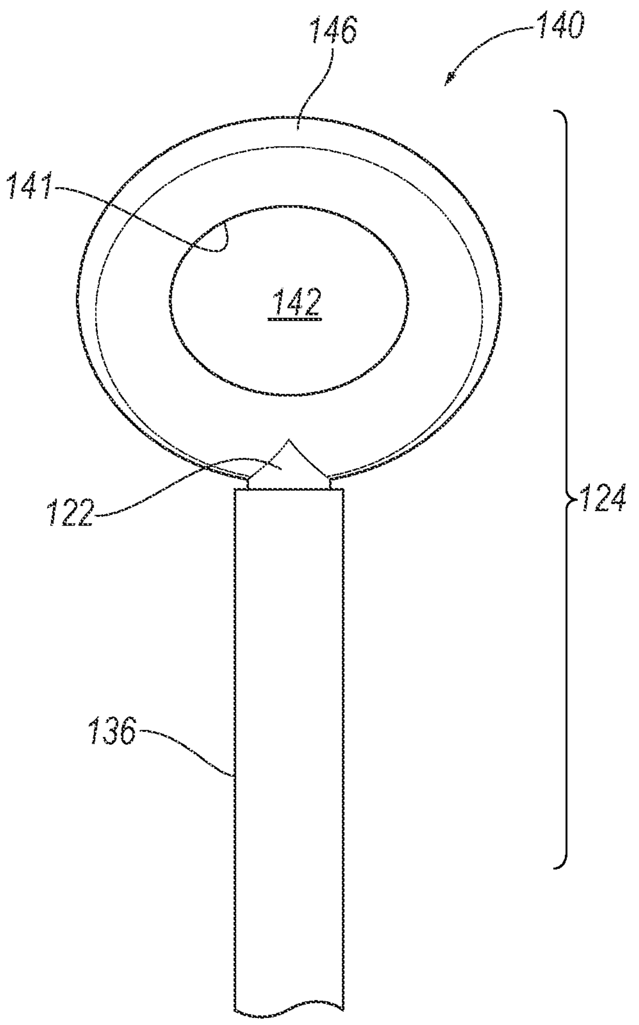
FIG. 6A is top view of an alternative exemplary arrangement of an electrode arrangement that may be utilized in the electrode system.
Figure 6B:
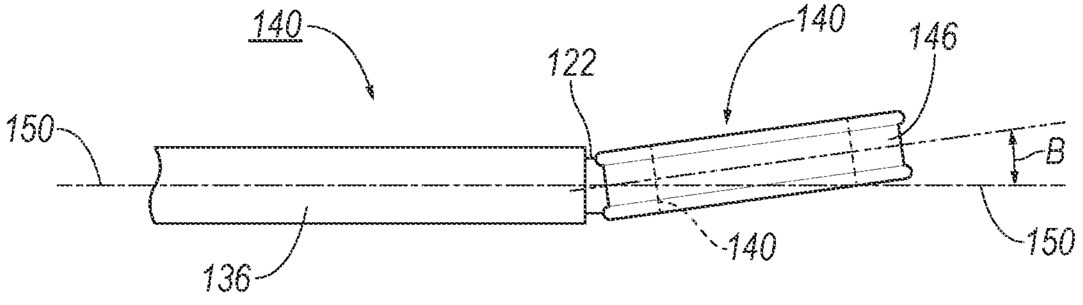
FIG. 6B is a side view of the electrode arrangement of FIG. 6A.

An alternative exemplary arrangement of an electrode arrangement 124 with an active electrode end 140 for use with the electrosurgical system 10 is shown in FIGS. 6A and 6B. The arrangement in FIGS. 6A-6B is similar as to the one shown in FIGS. 1-5 in that the electrode arrangement 124 includes an insulation sleeve 136 and a mounting shaft 138 similar to the mounting sleeve 36 and mounting shaft 38. However, instead of a concave active electrode end, the active electrode end 140 is circular with an opening 142 therethrough. The outer periphery of the active electrode end 140 may include an edge band 146 electrode. As with edge band 46, edge band 146 may also be provided with visual marker to indicate a depth of application when the active electrode end 140 is applied to tissue.

Referring to FIG. 6B, in one exemplary arrangement the active electrode end 140 is angled so as to have a distal-most end 148 extending upwardly, with respect to a central axis 150-150. For example, in one exemplary arrangement, the active electrode end 140 may be angled β upwardly in the range of 5-20 degrees. With this configuration, visibility of the active electrode end 140 will be increased during use.

Figure 7:
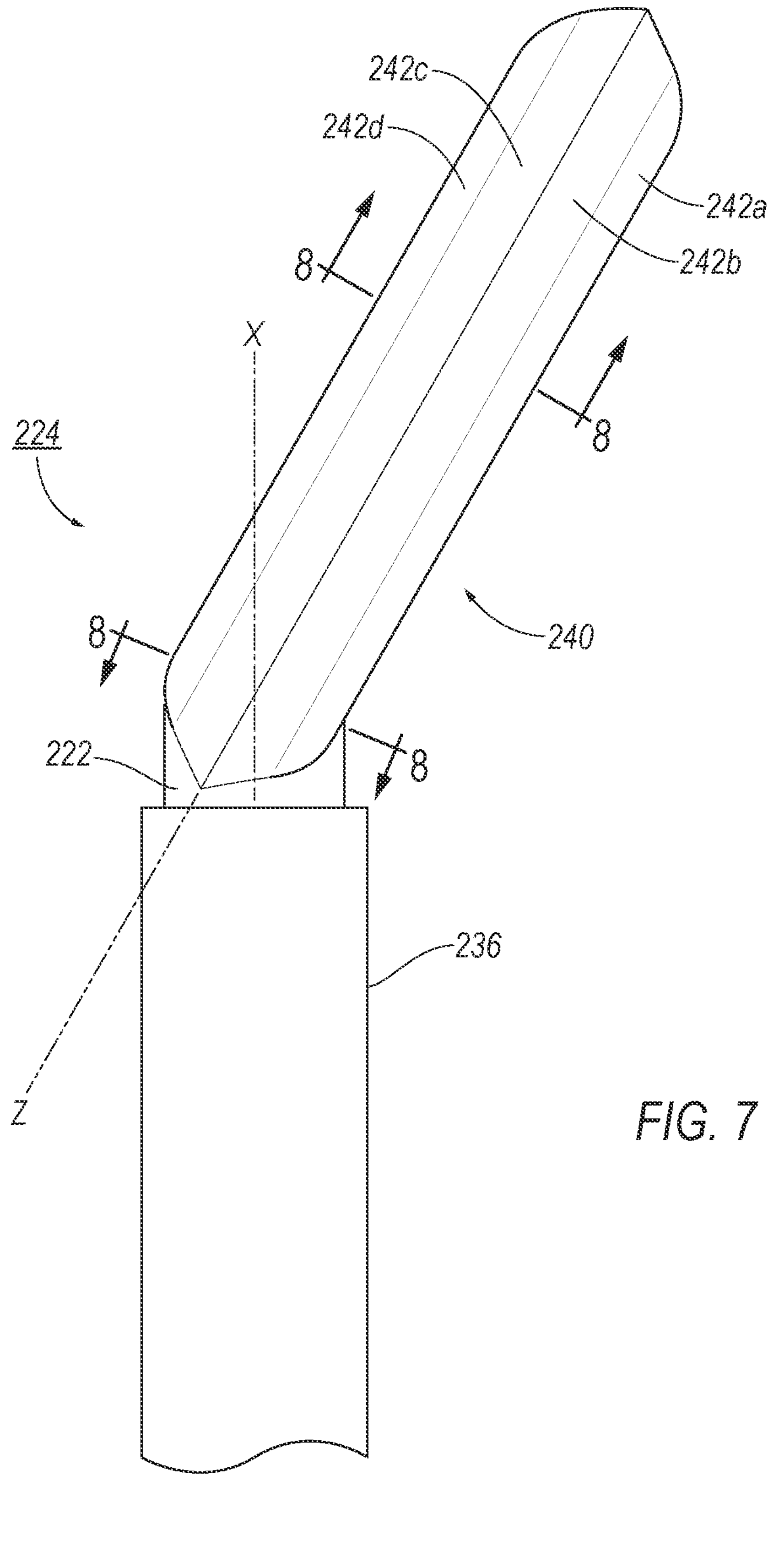
FIG. 7 is a further alternative exemplary arrangement of an electrode arrangement that may be utilized in the electrode system.

Referring to FIG. 7, a further alternative exemplary arrangement of an electrode arrangement 224 with an active electrode end 240 for use with the electrosurgical system 10 is shown in FIG. 7. The arrangement in FIG. 7 is similar as to the one shown in FIGS. 1-5 in that the electrode arrangement 224 includes an insulation sleeve 236 and a mounting shaft 222 similar to the insulation sleeve 36 and mounting shaft 22. However, instead of a concave active electrode end, the active electrode end 240 is constructed as a cantilever. In one exemplary arrangement, the cantilever end 240 may be constructed to extend from an angle from a central axis x-x extending through the mounting shaft 222, along an axis z-z.

Figure 8:
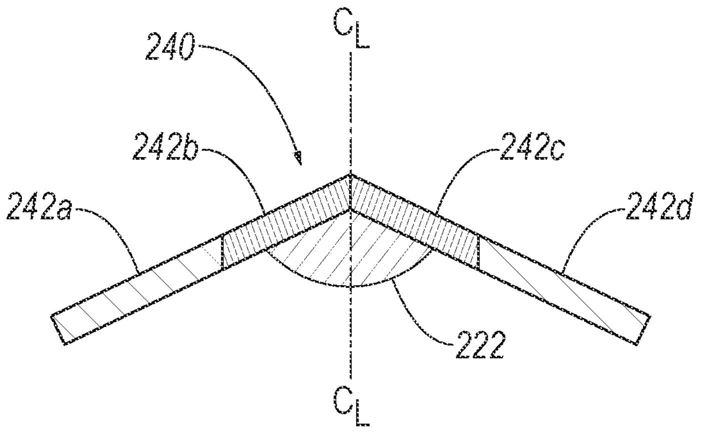
FIG. 8 is a cross sectional view of an active electrode end of the electrode arrangement of FIG. 7, taken along lines 8-8 in FIG. 7

In one exemplary arrangement, referring to FIG. 8, the active electrode end 240 is constructed so as to have a peaked configuration with positive and negative electrodes being disposed on either side of a center line CL which extends through the z-z axis. In one exemplary arrangement, the positive 242*a*, 242*c* and negative 242*b*, 242*d* electrodes are arranged in an alternating manner. In a further exemplary arrangement, the positive electrodes 242*a*, 242*c* are arrangement on one side of the center line, while the negative 242*b*, 242*d* electrodes are arranged on the opposite side of the center line. The outermost electrodes 242*a* and 242*d* may be both provided with visual markers to provide depth information when the active electrode end 240 is applied to tissue.

In the various exemplary arrangements, the insulation sleeve 36, 136, 236, is mounted around the mounting shaft 22, 122, and 222. For example, in one exemplary arrangement, the insulation sleeve 36, 136, 236 may be heat-shrunk about the electrode member arrangement 24, 124, 224.

The electrosurgical system 10 and the various exemplary arrangements may be used as follows in accordance with the exemplary arrangements of the disclosure. Using the exemplary arrangement shown in FIGS. 1-5, the electrosurgical system 10 and the electrode arrangements 24, 124, and 224 may be used to treat tissue of a patient. In one exemplary arrangement, the electrosurgical system 10 and the electrode arrangements 24, 124, and 224 may be used to electrosurgically vaporize and ablate tissue by contacting the respective active electrode ends 40, 140, and 240 with tissue while applying RF current from the electrosurgical apparatus 14 to the tissue through the electrode 100. The system 10 may be used in a controlled manner, such that the system 10 is suitable for delicate procedures, including, but not limited to cosmetic ablative procedures on skin tissue.

The active electrode ends 40, 140, 240 may be used in different operational modes, including a brushing mode, a cutting mode, and a scraping mode. More specifically, in some exemplary arrangements, the active electrode ends 40, 140, 240 may be energized so as to create an energized contact surface, which may be slid or brushed over a surface of exposed tissue such that the active electrode ends 40, 140, and 240 come into contact with the tissue to ablate a treated band of tissue. In a bushing operation, the active electrode ends 40, 140, 240 is dragged or slid by an operator, while in contact with the tissue, across an outer surface of the tissue. As the active electrode ends 40, 140, 240 brushes across the tissue, a layer of the tissue is ablated. In one exemplary arrangement, the treated band of tissue may be a relatively uniform depth across a width of the treated band. In some exemplary arrangements, the ablated tissue may be exposed surface tissue. In yet other exemplary arrangements, the ablated tissue is skin tissue. In further exemplary arrangements, the ablated tissue is gum tissue.

Figure 9:
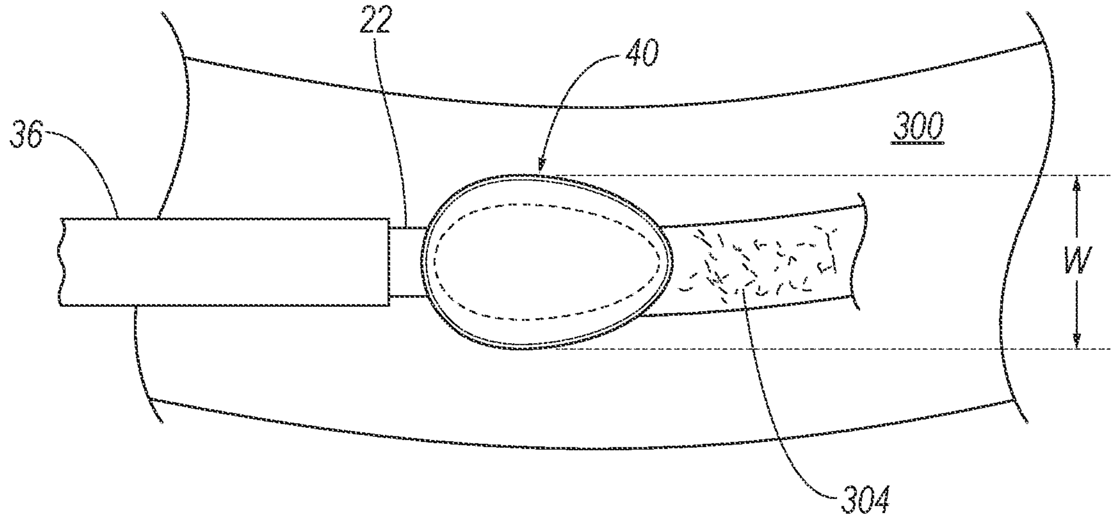
FIG. 9 is a top view of an electrode arrangement of FIG. 3 being used to execute a brushing step on a patient's gum tissue.
Figure 10:
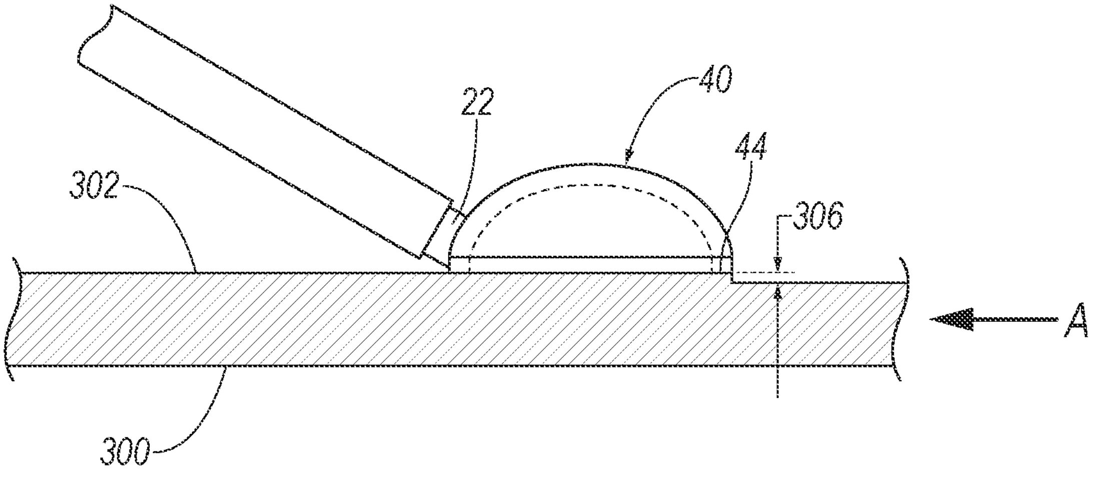
FIG. 10 is a partial cross-sectional view of the electrode arrangement of FIG. 3 as it is being applied to a patient's tissue.

Referring to FIGS. 9-10, illustrates the exemplary arrangement utilizing active electrode end 40 being slide or brushed across a surface 300 of a surface tissue 302 of a patient. The active electrode end 40 is placed in contact with the tissue surface 300. A contact edge 44 (best seen in FIG. 2) is maintained in contact with the tissue surface 300 while the contact edge 44 is displaced, or wiped across the tissue 302 of a patient in a direction A. Simultaneous with the brushing movement, the electrosurgical system 10 is operated to deliver RF energy to the active electrode end 40, as discussed above. Displacing the active electrode end 40 in this manner progressively advances the contact edge 43 to thereby create a swath or treated band 304 of treated tissue. In some exemplary arrangements, the electrode vaporizes and ablates a broad band of a layer of tissue and the treated band 304 is tissue from which overlying tissue has been vaporized and ablated.

Due to the shape of the exemplary arrangement of active electrode end 40, the contact edge 44 is arcuate when it comes into contact with the tissue 302, affording a broad contact area. Debris and excess removed tissue or saliva for those procedures involving the mouth, may be collected within the concave section of the active electrode end 40 (or within the opening 142 or trapped between wings of the angled active electrode end 240). The broad width of contact edge 44 serves to reduce surgical time, as less surgical passes are needed to clear an area. Indeed, in some exemplary arrangements, substantially all of an entire area of tissue within a treated band 304 is ablated by a brush stroke.

In some exemplary arrangements, a depth 306 (FIG. 10) of ablation across the width of the treated band 304 is substantially uniform. In other exemplary arrangements, the procedure includes executing a plurality of light pressure brush strokes over the tissue 300 to create a controlled and uniform depth 306 of tissue removal by ablation. While the bushing is shown as being performed in one direction A, it is understood that the active electrode end 40 may be moved in both directions.

In some exemplary arrangements, a width W of the contact edge 44 is in the range from about 1 mm to 4 mm. In one exemplary arrangements, the width W is substantially the same as the width of the treated band 304. In other exemplary arrangements, during application of the active electrode end 40, the active electrode end 40 may be applied at an angle to the tissue 300 such that only a portion of the contact edge 44 comes into contact tissue 300. In this manner, a width of the treated band 304 will be smaller than the total width W of the contact edge 44, a shown in FIG. 9, for example.

In further exemplary arrangements, the active electrode ends 40, 140, 240 may be used to cut and/or scrape tissue without the application of RF current. For example, the active electrode ends 40, 140, 240 may be used to scrape away tissue that has been desiccated or coagulated by the ablating step.

In some exemplary arrangements, the electrosurgical system 10 and the active electrode ends 40, 140, 240 can also be used to electrosurgically cut, scrape, cauterize, coagulate and/or desiccate tissue by contacting the active electrode ends 40, 140, 240 to the tissue.

In some exemplary arrangements, the mounting sections 22, 122, and 222 may be constructed to be bendable to customize the angle to the active electrode ends 40, 140, and 240 to the treatment, patient, or surgical step to be employed. Alternatively, there may be a malleable section 45 (see, e.g., FIG. 2) connected to the remainder of the mounting section 22, 122, 222 so as to be disposed between the remainder of the mounting section 22, 122, 222 and the active electrode ends 40, 140, 240, such that only that section may be bent or otherwise manipulated to different configurations to provide access to challenging locations. Accordingly, methods of using the system 10 may further include bending the active electrode ends 40, 140, 240 prior to use or between steps during a procedure.

In one exemplary arrangement, the system 10 and the active electrode ends 40, 140, 240 may be used in connection with various different exemplary scenarios. For example, the system 10 may be utilized to ablate gum tissue by vaporization. For example, in one exemplary arrangement, the system 10 is used to treat gingival hyperplasia. In some exemplary arrangements, the active electrode ends 40, 140, 240 is used to ablate a layer of gum tissue to effect a cosmetic treatment, for example to treat racial pigmentation. In yet another exemplary arrangement, the system 10 may be used to treat both gingival hyperplasia and racial pigmentation in the same procedure.

Figure 11:
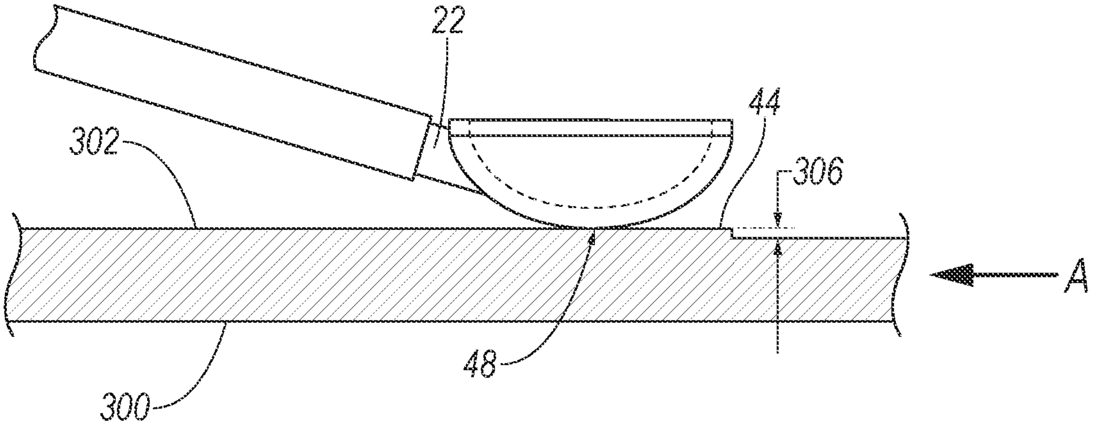
FIG. 11 is a partial cross-sectional view of the electrode arrangement of FIG. 3 as it is being applied to a patient's tissue in an alternative configuration.

In an alternative approach, for example, as shown in FIG. 11, the convex outer surface 48 of the active electrode end 40 may be applied to the surface tissue 302 such that the convex outer surface 48 may be used to wipe across tissue to ablate said surface tissue 302. With this arrangement, the operator is afforded the ability of increased control in that the convex outer surface 48 may be used in a brush manner, i.e., back and forth, a circular manner, or even in an up and down manner. This allows the ability for an operator to focus on specific areas for treatment.

For example, FIG. 11 illustrates the active electrode end 40 being slid or brushed against the surface 300 of the surface tissue 302 of a patient. The convex outer surface 48 is placed in contact with the tissue surface 300, while the active electrode 40 is displaced, or wiped across the tissue 302 of the patient in a direction A. However, as noted above, the convex outer surface 48 may be moved across the tissue surface 300 in other manners, such as in a circular manner or up and down, thereby allowing for different options for treatment. Movement of the convex outer surface 48 across the tissue 302 creates a treated band of tissue 304, similar to that discussed above in connection with FIGS. 9 and 10.

As explained above, a user may implement multiple strokes with the active electrode ends 40, 140, 240, as needed to ablate a desired region of tissue, such as gum tissue. For example, the user may continue to brush target tissue until most or substantially all of the target tissue has been ablated. Scraping or wiping steps may be executed between brush strokes to remove any residual tissue in order to clear the surgical field for further ablation or inspection. The user may alternate between the brushing and scraping steps as needed to progressively ablate and clear the target tissue.

More specifically, in some exemplary procedures, the user may use the brushing, scraping and/or wiping steps and techniques as follows:

In an initial step, a user prepares the system 10 for use. For example, in one exemplary arrangement, the electrode arrangement 24 may be a disposable element specifically designed for single patient use. Accordingly, the electrode arrangement 24 may be disposed within the handpiece 12 such that the electrode arrangement 24 is seated so as to be electrically connected to the electrical contact 28.

Once seated, the electrical cable 16 may be connected to the console generator 14. In one exemplary arrangement, the electrical cable 16 may be equipped with a "smart plug" 15. The smart plug 15 is configured only permit an output suitable for the handpiece 12. An example of such an arrangement is disclosed in U.S. Pat. No. 6,994,707, the contents of which are incorporated by reference. Accordingly, when the smart plug is connected to the console generator 14, and the console generator 14 is turned on, the handpiece 12 may impart RF energy to the electrode arrangement 24 when an activation switch 31 (see FIG. 1) is activated such that the electrode arrangement 24 is energized.

Once energized, the user may brush the tissue surface. For example, when utilizing the system 10 to treat gum tissue, the active electrode end 40, 140, 240 is applied to gum tissue, i.e., a brushing operation is applied to the gum tissue to vaporize or ablate the target tissue. The user will take care not to unintentionally contact and ablate tissue that does not need treatment. To avoid such unintentional contact, the user will visually monitor lateral edges of the of the active electrode ends 40. 140, 240 as they are positioned on the tissue. Depth of ablation may also be observed using visual observation as well.

After the brushing operation, the electrode assembly 24, 124, 224 may be de-energized by deactivating the handpiece 12 through the switch 31. Once deactivated, the user may scrape residual tissue from the ablative operation (e.g. coagulated collagen or other tissue) using various edges 46, 146, 246 of the surgical system 10. For example, in the exemplary arrangement that utilizes the active electrode end 40, the edges 46 may be used to scoop the residual tissue into the concave area to direct the tissue out of the surgical area. In connection with the exemplary arrangement that utilizes the active electrode end 140, an inner peripheral edge 141 may be used to pull the residual tissue into the opening 142 such that the residual tissue may be pulled out of the surgical area. As another example, with respect to the exemplary arrangement shown in FIGS. 7-8, the active electrode end 240 may be angled and dragged to collect the residual tissue. As the active electrode end 240 is configured with an angled configured (best seen in FIG. 8), the tissue will collect within the electrode end 240 as it is moved.

After the scraping/wiping procedure described above, the handpiece 12 may be turned back on and the procedure outlined above may be repeated. In addition, the procedure may include executed a plurality of brush strokes over the target tissue to create a controlled and uniform depth of tissue removal by ablation. The brushing operation can occur in both direction or in a single directions.

It will be appreciated that the systems and methods described herein have broad applications. The foregoing embodiments were chosen and described in order to illustrate principles of the methods and systems as well as some practical applications. The preceding description enables others skilled in the art to utilize methods and systems in various embodiments and with various modifications as are suited to the particular use contemplated. In accordance with the provisions of the patent statutes, the principles and modes of operation of this disclosure have been explained and illustrated in exemplary arrangements.

It is intended that the scope of the present methods and arrangements be defined by the following claims. However, it must be understood that this disclosure may be practiced otherwise than is specifically explained and illustrated without departing from its spirit or scope. It should be understood by those skilled in the art that various alternatives to the arrangements described herein may be employed in practicing the claims without departing from the spirit and scope as defined in the following claims. The scope of the disclosure should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

The invention claimed is:

1. An electrosurgical system, comprising:

a handpiece having a mounting channel therein, an electrical contact in communication with the mounting channel;

an electrode arrangement that is engageable within the mounting channel;

wherein the electrode arrangement further comprises a mounting shaft that is in communication with an active electrode end, wherein the active electrode end is configured to deliver RF energy when the mounting shaft is in electrical engagement with the electrical contact within the mounting channel and the handpiece is in an energized state; and wherein the active electrode end is configured to be concave shaped, defining an outer convex surface, with the edge portion being disposed about the periphery of the active electrode end;

wherein the entire active electrode conducts RF energy;

wherein the mounting shaft extends from the outer convex surface at a location approximately 45 degrees between an apex of the convex surface and a surface defined by the edge portion;

wherein the mounting shaft has an angle of approximately 45 degrees from the surface defined by the edge portion;

wherein the location of the mounting shaft and the angle of the mounting shaft allow a user to position the convex surface flat against a surface.

2. The electrosurgical system of claim 1, wherein the active electrode is in the shape of an oval.

3. The electrosurgical system of claim 1, further comprising an insulating sleeve disposed over the mounting shaft, wherein a proximal end of the mounting shaft extends outwardly from the insulating sleeve when mounted on the mounting shaft, wherein the insulating sleeve is received within the mounting channel.

4. The electrosurgical system of claim 3, wherein the insulating sleeve is heat-shrinked about the mounting shaft.

5. The electrosurgical system of claim 1, wherein the mounting shaft further includes a pair of mounting grooves that cooperate with a locking element disposed on a distal end of the handpiece to lock the electrode arrangement within the handpiece.

6. The electrosurgical system of claim 5, wherein the electrical contact is a constructed as a tubular member disposed within the mounting channel so as to encircle a proximal end of the mounting shaft, when the mounting shaft is seated within the mounting channel.

7. The electrosurgical system of claim 1, further comprising a console generator that is configured to power the handpiece, wherein the console generator connects to the handpiece via an electrical cable, wherein a first end of the electrical cable is connected to an electrical contact disposed within the handpiece.

8. The electrosurgical system of claim 7, wherein the electrical cable is selectively connected to the electrical contact within the handpiece.

9. The electrosurgical system of claim 7 wherein a second end of the electrical cable further comprises a smart plug that operatively limits the electrical output to the handpiece from the console generator.

10. A method of applying an active electrode end according to claim 1, to a tissue surface, comprising applying the bottom convex surface to tissue and moving the active electrode end across the tissue surface.

* * * * *